US005658803A

United States Patent [19]

Kuo

[11] Patent Number: 5,658,803
[45] Date of Patent: Aug. 19, 1997

[54] MONOCLONAL ANTIBODIES REACTIVE WITH CACHECTIN

[75] Inventor: George Kuo, San Francisco, Calif.

[73] Assignee: Chiron Corporation, Emeryviille, Calif.

[21] Appl. No.: 351,553

[22] Filed: Dec. 6, 1994

Related U.S. Application Data

[63] Continuation of Ser. No. 936,525, Aug. 28, 1992, abandoned, which is a continuation of Ser. No. 220,206, Jul. 18, 1988, abandoned.

[51] Int. Cl.$^6$ .................. G01N 33/536; C07K 16/22; C07K 16/24; C12N 5/20
[52] U.S. Cl. .................. 436/536; 435/70.21; 435/335; 436/548; 530/388.24; 530/391.3; 530/388.23
[58] Field of Search ................ 424/141.1, 145.7, 424/156.1, 158.1, 198.1; 435/7.92, 70.21, 172.2, 240.27; 436/512, 542, 548, 536; 530/387.1, 388.23, 388.24, 389.2, 395, 391.3

[56] References Cited

U.S. PATENT DOCUMENTS

| 4,603,106 | 7/1986 | Cerami et al. | 435/7.92 |
|---|---|---|---|
| 4,684,623 | 8/1987 | Larrick et al. | 514/12 |
| 4,834,976 | 5/1989 | Rosok et al. | 424/87 |
| 4,870,163 | 9/1989 | Rubin et al. | 530/413 |
| 5,231,024 | 7/1993 | Moeller et al. | 435/240.27 |

FOREIGN PATENT DOCUMENTS

| 260610 | 3/1988 | European Pat. Off. |
| WO87/03489 | 6/1987 | WIPO . |

OTHER PUBLICATIONS

Pennica, et al., "Human Tumour Necrosis Factor: Precursor Structure, Expression and Homology to Lymphotoxin," Nature (1984), 312:724–728.

Shirai, et al., "Cloning and Expression in *E. Coli* of the Gene for Human Tumour Necrosis Factor," Nature (1985), 313:803–806.

Beutler, et al., "Passive Immunization Against Cachectin/Tumor Necrosis Factor Protects Mice from Lethal Effect of Endotoxin," Science (1985), 229:869–871.

Liang, et al., "Production and Characterization of Monoclonal Antibodies Against Recombinant Human Tumor Necrosis Factor/Cachectin," Biochem. Biophys. Res. Comm. (1986) 137:847–854.

Fendly, et al., "Murine Monoclonal Antibodies Defining Neutralizing Epitopes on Tumor Necrosis Factor," Hybridoma (1987) 6:359–370.

Hirai, et al., "Production and Characterization of Monoclonal Antibodies to Human Tumor Necrosis Factor," J. Immunol. Meth. (1987) 96:57–62.

Beutler, et al., "Cachectin: More Than A Tumor Necrosis Factor," New Eng. J. Med. (1987), 316:379–385.

Tsujimoto, et al., "Comparative Studies of the Biological Activities of Human Tumor Necrosis Factor and Its Derivatives," J. Biochem. (1987), 101:919–925.

Tracey, et al., "Anti–Cachectin/TNF Monoclonal Antibodies Prevent Septic Shock During Lethal Bacteraemia," Nature (1987) 330:662–664.

Mathison, et al., "Participation of Tumor Necrosis Factor in the Mediation of Gram Negative Bacterial Lipopolysaccharide–Induced Injury in Rabbits," J. Clin. Invest. (1988), 81:1925–1937.

Michie, et al., "Detection of Circulating Tumor Necrosis Factor After Endotoxin Administration," New Eng. J. Med. (1988) 318:1481–1486.

Hinshaw, et al., "Current Management of the Septic Shock Patient: Experimental Basis for Treatment," Circulatory Shock (1982) 9:543–553.

Waldmann, T.A., "Monoclonal Antibodies in Diagnosis and Therapy," Science 252: 1657–1662, 21 Jun. 1991.

Fitzer–Schiller, G., "Centocor Stops Trials of Flagship Drug," *Washington Post*, 19 Jan. 1993.

Harris et al, "Therapeutic Antibodies—The Coming of Age", *Trends in Biotechnology* 11:42–44, Feb. 1993.

Abramowicz, D., et al., "Anaphylactic Shock After Treatment With OKT3 Monoclonal Antibody", *New England J. Med.*, 3 Sep. 1992, p. 736.

Cross et al., "Choice of Bacteria in Animal Models of Sepsis," *Infection and Immunity* 61(7):2741–2747, Jul. 1993.

Hesse et al., "Cytokine Appearance in Human Endotoxemia and Primate Bacteremia," *Surg. Gynecol. Obstet.* 166(2):147–153, 1988.

*Primary Examiner*—Robert D. Budens
*Attorney, Agent, or Firm*—Roberta L. Robins; Pauul B. Savereide; Robert P. Blackburn

[57] ABSTRACT

Cell lines are provided that produce improved neutralizing monoclonal antibodies reactive with human cachectin. The antibodies have various therapeutic and diagnostic uses.

10 Claims, No Drawings

MONOCLONAL ANTIBODIES REACTIVE WITH CACHECTIN

CROSS-REFERENCE TO RELATED APPLICATION

This application is a continuation of U.S. Ser. No. 07/936,525, filed Aug. 28, 1992, now abandoned, which is a continuation of U.S. Ser. No. 07/220,206, filed Jul. 18, 1988, now abandoned. Priority is hereby claimed under 35 USC §120 and these applications are incorporated by reference in their entirety.

BACKGROUND OF THE INVENTION

The introduction of invasive stimuli, such as parasitic, bacterial or viral infections, or neoplastic cells, induce significant metabolic changes in the susceptible host. If serious, the changes may eventually disrupt normal homeostatic mechanisms, both locally and systemically, leading to the depletion of host energy stores advancing to wasting (Cachexia), tissue damage, multiple organ system failure, shock and death.

Until recently, clinicians believed that the systematic patterns were primarily due to actions of the invasive agents themselves. However, it is now known that the invasive stimuli cause the host to generate various cytokines, the combined actions of which cause most of the undesirable biological responses. These host-derived inflammatory mediators present new opportunities for developing treatment regimens against a wide variety of inflammatory disease states.

One of the most potent cytokines is cachectin, which is primarily released by macrophages after appropriate stimulation. Cachectin, also known as Tumor Necrosis Factor, is a protein having 157 amino acids normally found in vivo as a dimer or other multimer. The calculated molecular weight of human TNF monomer is about 17,000 daltons.

Cachectin acts to suppress biosynthesis of several adipocyte-specific proteins, such as lipoprotein lipase. It also acts to induce the biosynthesis or release of numerous other proteins, including Class I major histocompatibility antigen, granulocyte-macrophage-colony stimulating factor, and interleukin 1. (See, generally, Beutler and Cerami, *New Eng. J. of Med.*, 316:379-385 (1987), which is incorporated herein by reference.)

The recognition of cachectin's broad influence on various disease states has led to attempts in controlling its actions. For example, experiments have shown that antibodies specifically reactive with cachectin may be therapeutically useful in controlling the immunomodulatory responses now known to be associated with cachectin (see, U.S. Pat. Nos. 4,603,106 and 4,684,623, both of which are incorporated herein by reference). In particular, neutralizing antibodies capable of binding various epitopes on human cachectin at high affinity have significant potential for mediating the toxic effects of excess cachectin levels.

Thus, there exists a need for improved antibodies capable of neutralizing the toxic effects of cachectin in vivo. The present invention fulfills these needs.

SUMMARY OF THE INVENTION

Novel cell lines are provided which produce monoclonal antibodies capable of binding to human cachectin epitopes with enhanced neutralization capability in vivo. Additionally, methods are provided for treating a human susceptible to bacteremia or sepsis or already infected with an endotoxin-bearing bacteria by administering a prophylactic or therapeutic amount of a composition comprising at least one monoclonal antibody or binding fragment thereof capable of reacting with human cachectin and exhibiting neutralizing activity in an L929 cell cytolytic assay at less than about 400 ng, typically between about 50 to 200 ng or more, the composition preferably further including a physiologically acceptable carrier. The composition may also contain any one or more of the following: additional monoclonal antibodies capable of reacting with bacterial endotoxins or exotoxins; monoclonal antibodies capable of reacting with serotype determinants on particular bacterial strains bearing endotoxins; a gamma globulin fraction from human blood plasma, where the plasma may be obtained from a human exhibiting elevated levels of immunoglobulins reactive with bacterial endotoxins; and one or more antimicrobial agents. Further, clinical uses of the monoclonal antibodies are provided, including the production of diagnostic kits.

DESCRIPTION OF THE SPECIFIC EMBODIMENTS

In accordance with the present invention, novel cells capable of producing neutralizing monoclonal antibodies of desired affinities and compositions comprising such antibodies are provided, such compositions being capable of selectively recognizing epitopes present on human cachectin. The subject cells have identifiable chromosomes in which the germ-line DNA from them or a precursor cell has rearranged to encode an antibody having a binding site for a desired epitope on human cachectin. These monoclonal antibodies can be used in a wide variety of ways, including diagnosis and therapy.

The monoclonal antibodies so provided are particularly useful, when compared to prior art antibodies, in the treatment or prophylaxis of serious diseases, such as bacteremia, sepsis, cachexia, or other disease states associated with elevated levels of cachectin. Thus, the antibodies will typically have neutralizing activity at less than 400 ng, preferably less than about 300 ng, most preferably about 50 to 200 ng, in the L929 cell cytolytic assay. This higher level of activity permits utilizing significantly lower dosage levels for treatments.

The preparation of monoclonal antibodies can be accomplished by immortalizing a cell line capable of expressing nucleic acid sequences that code for antibodies specific for an appropriate epitope on human cachectin. The immortalized cell line may be a mammalian cell line that has been transformed through oncogenesis, by transfection, mutation, or the like. Such cells include myeloma lines, lymphoma lines, or other cell line capable of supporting the expression and secretion of the immunoglobulin, or binding fragment thereof, in vitro. The immunoglobulin or fragment may be a naturally-occurring immunoglobulin of a mammal other than the preferred mouse or human sources, produced by transformation of a lymphocyte, particularly a splenocyte, by means of a virus or by fusion of the lymphocyte with a neoplastic cell, e.g., a myeloma, to produce a hybrid cell line. Typically, the splenocyte will be obtained from an animal immunized against cachectin-related antigens or fragments thereof containing an epitopic site. Immunization protocols are well known and can vary considerably yet remain effective. (See, Goding, *Monoclonal Antibodies: Principles and Practice*, 2d Ed., Academic Press, N.Y. [1986], which is incorporated herein by reference.)

The hybrid cell lines may be cloned and screened in accordance with conventional techniques, and antibodies in the cell supernatants detected that are capable of binding to the desired human cachectin determinants with appropriate affinities. The appropriate hybrid cell lines may then be grown in large-scale culture or injected into the peritoneal cavity of an appropriate host for production of antibodies ascites fluid.

By virtue of having the antibodies of the present invention, which are known to be specific for the human cachectin protein, in some cases the supernatants of subsequent experiments may be screened in a competition assay with the subject monoclonal antibodies as a means to identify additional examples of the desired anti-human cachectin monoclonal antibodies (so-called "blocking antibodies"). Thus, hybrid cell lines can be readily produced from a variety of sources based on the availability of present antibodies specific for the particular cachectic determinants at the appropriate affinity levels.

Alternatively, where hybrid cell lines are available that produce antibodies specific for the subject epitopic sites, these hybrid cell lines may be fused with other neoplastic B-cells, where such other B-cells may serve as recipients for genomic DNA coding for the antibodies. These antibodies may be functional at the cell surface and not, for example, as receptors. While rodent, particularly murine, neoplastic B-cells are most commonly utilized, other mammalian species may be employed, such as lagomorpha, bovine, ovine, equine, porcine, avian or the like.

The monoclonal antibodies may be of any of the classes or subclasses of immunoglobulins, such as IgM, IgD, IgA, IgE, or subclasses of IgG known for each species of animal. Generally, the monoclonal antibodies may be used intact, or as binding fragments, such as Fv, Fab, F(ab')$_2$, but usually intact.

The cell lines of the present invention may find use other than for the direct production of the monoclonal antibodies. The cell lines may be fused with other cells (such as suitably drug-marked human myeloma, mouse myelomas or human lymphoblastoid cells) to produce hybridomas or triomas, and thus provide for the transfer of the genes encoding the monoclonal antibodies. Alternatively, the cell lines may be used as a source of the chromosomes encoding the immunoglobulins, which may be isolated and transferred to cells by techniques other than fusion. In addition, the genes encoding the monoclonal antibodies may be isolated and used in accordance with recombinant DNA techniques for the production of the specific immunoglobulin in a variety of hosts. Particularly, by preparing cDNA libraries from messenger RNA, a single cDNA clone, coding for the immunoglobulin and free of introns, may be isolated and placed into suitable prokaryotic or eukaryotic expression vectors and subsequently transformed into a host for ultimate bulk production. (See, generally, U.S. Pat. Nos. 4,172,124; 4,350, 683; 4,363,799; 4,381,292; and 4,423,147. See also, Kennett, et al., *Monoclonal Antibodies*, Plenum, New York [1980], and references cited therein, al of which are incorporated herein by reference.)

More specifically, in accordance with hybrid DNA technology, the immunoglobulins or fragments of the present invention may be produced in bacteria or yeast. (See, Boss, et al., *Nucl. Acid. Res.*, 12:3791 and Wood, et al., *Nature* 314:446, both of which are incorporated herein by reference.) For example, the messenger RNA transcribed from the genes coding for the light and heavy chains of the monoclonal antibodies produced by a cell line of the present invention may be isolated by differential cDNA hybridization employing cDNA from BALB/c lymphocytes other than the subject clone. The mRNA that does not hybridize will be rich for the message coding for the desired immunoglobulin chains. As necessary, this process can be repeated to further enhance the desired mRNA levels. The subtracted mRNA composition may then be reverse-transcribed to provide for a cDNA mixture enriched for the desired sequences. The RNA may be hydrolyzed with an appropriate RNAse and the ssDNA made double-stranded with DNA polymerase I and random primers, e.g., randomly fragmented calf thymus DNA. The resulting dsDNA may then be cloned by insertion into an appropriate vector, e.g., virus vectors, such as lambda vectors or plasmid vectors (such as pBR322, pACYC184, etc.). By developing probes based on known sequences for the constant regions of the light and heavy chains, those cDNA clones having the gene coding for the desired light and heavy chains can be identified by hybridization. Thereafter, the genes may be excised from the plasmids, manipulated to remove superfluous DNA upstream from the initiation codon or constant region DNA, and then introduced in an appropriate vector for transformation of a host and ultimate expression of the gene.

Conveniently, mammalian hosts (e.g, mouse cells) may be employed to process the chain (e.g., join the heavy and light chains) to produce an intact immunoglobulin, and furthermore, secrete the immunoglobulin free of the leader sequence, if desired. Alternatively, one may use unicellular microorganisms for producing the two chains, where further manipulation may be required to remove the DNA sequences coding for the secretory leader and processing signals, while providing for an initiation codon at the 5' terminus of the sequence coding for the heavy chain. In this manner, the immunoglobulins can be prepared and processed so as to be assembled and glycosylated in cells other than mammalian cells. If desired, each of the chains may be truncated so as to retain at least the variable region, which regions may then be manipulated to provide for other immunoglobulins or fragment specific for the cachectin epitopes (see, e.g., European patent application publication numbers 0239400 and 0125023, which are incorporated herein by reference).

The monoclonal antibodies of the present invention are particularly useful because of their high affinity for epitopes of human cachectin. Also, some of the monoclonal antibodies are protective in vivo, permitting incorporation into pharmaceutical products, such as antibody combinations for bacterial infections.

Monoclonal antibodies of the present invention can also find a wide variety of utilities in vitro. By way of example, the monoclonal antibodies can be utilized for purifying native or recombinant human cachectin, for selectively removing human cachectin in a heterogeneous mixture of proteins, or the like.

For diagnostic purposes, the monoclonal antibodies may either be labeled or unlabeled. Typically, the diagnostic assays entail detecting the formation of a complex through the binding of the monoclonal antibody to the protein. When unlabeled, the antibodies find use in agglutination assays. In addition, unlabeled antibodies can be used in combination with other labeled antibodies (second antibodies) that are reactive with the monoclonal antibody, such as antibodies specific for immunoglobulin. Alternatively, the monoclonal antibodies can be directly labeled. A wide variety of labels may be employed, such as radionuclides, fluorescers, enzymes, enzyme substrates, enzyme cofactors, enzyme inhibitors, ligands (particularly haptens), etc. Numerous types of immunoassays are available, and by way of example, some include those described in U.S. Pat. Nos.

3,817,827; 3,850,752; 3,901,654; 3,935,074; 3,984,533; 3,996,345; 4,034,074; and 4,098,876, all of which are incorporated herein by reference.

Commonly, the monoclonal antibodies of the present invention are utilized in enzyme immunoassays, where the subject antibodies, or second antibodies from a different species, are conjugated to an enzyme. When a sample containing human cachectin, such as human blood or lysate thereof, is combined with the subject antibodies, binding occurs between the antibodies and those molecules exhibiting the desired epitope. Such complexes may then be separated from the unbound reagents, and a second antibody (labeled with an enzyme) added. Thereafter, the presence of the antibody-enzyme conjugate specifically bound to the cells is determined. Other conventional techniques well known to those skilled in the art may also be utilized.

Kits can also be supplied for use with the subject antibodies for detecting human cachectin in solutions or the presence of human cachectin epitopes in recombinant fractions. Thus, the subject monoclonal antibody composition of the present invention may be provided, usually in a lyophilized form, either alone or in conjunction with antibodies specific for endotoxins, exotoxins or gram-negative bacteria. The antibodies, which may be conjugated to a label or unconjugated, are included in the kits with buffers, such as Tris, phosphate, carbonate, etc., stabilizers, biocides, inert proteins, e.g., bovine serum albumin, or the like. Generally, these material will be present in less than about 5% wt. based on the amount of active antibody, and usually present in total amount of at least about 0.001% wt. based again on the antibody concentration. Frequently, it will be desirable to include an inert extender or excipient to dilute the active ingredients, where the excipient may be present in from about 1 to 99% wt. of the total composition. Where a second antibody capable of binding to the monoclonal antibody is employed, this will usually be present in a separate vial. The second antibody is typically conjugated to a label and formulated in an analogous manner with the antibody formulations described above.

The monoclonal antibodies of this invention can also be incorporated as components of pharmaceutical compositions containing a therapeutic or prophylactic amount of at least one, but commonly a mixture comprising two or more, of the monoclonal antibodies of this invention with a pharmaceutically effective carrier. A pharmaceutical carrier should be any compatible, non-toxic substance suitable to deliver the monoclonal antibodies to the patient. Sterile water, alcohol, fats, waxes, and inert solids may be used as the carrier. Pharmaceutically accepted adjuvants (buffering agents, dispersing agents) may also be incorporated into the pharmaceutical composition. Such compositions can contain monoclonal antibodies specific only for human cachectin. Alternatively, a pharmaceutical composition can contain monoclonal antibodies reactive directly with bacteria can be utilized to form a "cocktail." For example, a cocktail containing monoclonal antibodies against human cachectin epitopes and against groups of the various bacterial strains (e.g., different serotypes) causing sepsis would be a universal product with activity against the great majority of the clinical isolates responsible for the disease.

The mole ratio of the various monoclonal antibody components will usually not differ by more than a factor of 10, more usually by not more than a factor of 5, and will usually be in a mole ratio of about 1:1–2 to each of the other antibody components. When used in combination, the monoclonal antibodies of the present invention will be generally used in equal molor ratios.

The monoclonal antibodies of the present invention may also be used in combination with existing blood plasma products, such as commercially available gamma globulin and immune globulin products used in prophylactic or therapeutic treatment of bacterial sepsis in humans. Preferably, for immune globulins the plasma will be obtained from human donors exhibiting elevated levels of immunoglobulins reactive with endotoxin bearing bacteria. (See, generally, the compendium "Intravenous Immune Globulin and the Compromised Host," *Amer. J. Med.*, 76(3a), Mar. 30, 1984, pp.1–231, which is incorporated herein by reference.)

The monoclonal antibodies can also be used as separately administered compositions given in conjunction with antibiotics or antimicrobial agents. Typically, the antimicrobial agents may include a penicillin in conjunction with an aminoglycoside (e.g., gentamicin, tobramycin, etc.), but numerous additional agents (e.g., cephalosporins) well-known to those skilled in the art may also be utilized.

The monoclonal antibodies and pharmaceutical compositions thereof of this invention are particularly useful for oral or parenteral administration. Preferably, the pharmaceutical compositions may be administered parenterally, i.e., subcutaneously, intramuscularly, intraarterially or intravenously. Thus, this invention provides compositions for parenteral administration which comprise a solution of the monoclonal antibody or a cocktail thereof dissolved in an acceptable carrier, preferably an aqueous carrier. A variety of aqueous carriers can be used, e.g., water, buffered water, 0.4% saline, 0.3% glycine and the like. These solutions are sterile and generally free of particulate matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example sodium acetate, sodium chloride, potassium chloride, calcium chloride, sodium lactate, etc. The concentration of antibody in these formulations can vary widely, i.e., from less than about 0.5%, usually at or at least bout 1% to as much as 15 or 20% by weight and will be selected primarily based on fluid volumes, viscosities, etc., preferably for the particular mode of administration selected.

Thus, a typical pharmaceutical composition for intramuscular injection could be made up to contain 1 ml sterile buffered water, and 500 mg of monoclonal antibody. A typical composition for intravenous infusion could be made up to contain 250 ml of sterile Ringer's solution, and 150 mg of monoclonal antibody. Actual methods for preparing parenterally administrable compositions will be known or apparent to those skilled in the art and are described in more detail in, for example, *Remington's Pharmaceutical Science*, 15 Ed., Mack Publishing Company, Easton, Pa. (1980), which is incorporated herein by reference.

The monoclonal antibodies of this invention can be lyophilized for storage and reconstituted in a suitable carrier prior to use. This technique has been shown to be effective with conventional immune globulins and art-known lyophilization and reconstitution techniques can be employed. It will be appreciated by those skilled in the art that lyophilization and reconstitution can lead to varying degrees of antibody activity loss (e.g., with conventional immune globulins, IgM antibodies tend to have greater activity loss than IgG antibodies) and that use levels may have to be adjusted to compensate.

The compositions containing the present monoclonal antibodies or a cocktail thereof can be administered for the prophylactic and/or therapeutic treatment of any of a variety of bacterial infections. In therapeutic application, compositions are administered to a patient already infected with one or more bacterial strains in an amount sufficient to cure or at least partially arrest the infection and its complications. An amount adequate to accomplish this is defined as a "therapeutically effective dose." Amounts effective for this will depend upon the severity of the infection and the general state of the patient's own immune system, but generally range from about 1 to about 200 mg of antibody per kilogram of body weight with dosages of from 5 to 25 mg per kilogram being more commonly used. It must be kept in mind that the materials of this invention may generally be employed in serious disease states, that is, life-threatening or potentially life-threatening situations, especially bacteremia and endotoxemia.

In prophylactic applications, compositions containing the present antibody or a cocktail thereof are administered to a patient not already infected to enhance the patient's resistance to potential infections. Such an amount is defined to be a "prophylactically effective does." In this use, the precise amounts again depend upon the patient's state of health and general level of immunity, but generally range from 0.1 to 25 mg per kilogram, especially 0.5 to 2.5 mg per kilogram.

Single or multiple administrations of the compositions can be carried out with dose levels and pattern being selected by the treating physician. In any event, the pharmaceutical formulations should provide a quantity of the antibody(ies) of this invention sufficient to effectively treat or prophylax the patient.

EXPERIMENTAL

Production and Purification of Cachectin

Recombinant human cachectin (Pennica, et al., *Nature*, 312:724–729 (1984) and Shirai, et al., *Nature*, 313:803–806 (1985), both of which are incorporated herein by reference) was expressed as an intracellular protein in yeast from a synthetic gene encoding an initiation methionine and the sequence of mature cachectin, with codons chosen to reflect that of highly expressed yeast genes in accordance with standard techniques. The Synthetic sequences were placed downstream from a hybrid alcohol dehydrogenase/glyceraldehyde-3-phosphate dehydrogenase (ADH2/GAPDH) promoter. Cachectin synthesis was induced in transformed cultures of *Saccharomyces cerevisiae* by glucose deprivation. About 5–10% of total yeast protein was cachectin.

The cachectin was purified from crude yeast extracts by (a) Ammonium sulfate fractionation, (b) Q-Sepharose Fast Flow Column Chromatography, (c) S-Sepharose Fast Flow Column Chromatography, and (d) Sepharcryl S-200 (HR) Column Chromatography.

This procedure gave about 80% recovery of cachectin activity as assayed with actinomycin D-treated L929 cells (Ruff and Gifford, (1981) *Tumor Necrosis Factor, Lymphokines*, 2:235–272). The specific activity of purified cachectin was $2-4 \times 10^8$ units/mg, and the purity greater than 98% as judged by SDS polyacrylamide gel electrophoresis.

Production of Monoclonal Antibodies to Cachectin

BALB/c mice were immunized intraperitoneally with 5 to 25 µg Freund's complete adjucant, and boosted twice with the same dose in Freund's incomplete adjuvant at 3 weekly intervals. A final intraperitoneal boost of the same dose in aqueous solution was given, and the fusion performed 3 to 4 days later.

Spleen cells (about $10^8$ cells) from immunized mice were fused with about $2 \times 10^7$ myeloma cells (P3-X63-Ag8.653) (Kearney et al., *J. Immunol.* (1979) 123:1548–1550) using polyethylene glycol according to Kohler and Milstein (*Nature* 256:495 (1979)). The cells were plated in microtiter plates, and the hybrids were selected by hypoxanthine aminopterin thymidine (HAT) medium.

Five fusions were performed with spleen cells from five mice immunized with cachectin. By using the solid phase enzyme-linked immunosorbent assays, 60 positive clones were obtained producing monoclonal antibodies to cachectin.

The hybrids from positive wells were cloned 3 times by limit dilutions to make certain that each was a true clone. Fourteen hybridomas positive for cachectin were cloned and characterized.

Cachectin/TNF Bioassay: L-929 Cell Cytotoxicity

TNF activity was measured using a cytolytic assay with actinomycin D-treated L929 cells as described by Ruff and Gifford in *Lymphokines* 2:235, (1981), which is incorporated herein by reference.

L929 cells (CCL1, American Type Culture Collection, Rockville, Md.) are maintained in RPMI 1640 supplemented with 10 mM Hepes and 10% fetal bovine serum (or DME+ 10% FBS). Confluent cultures ($3-4 \times 10^7$ cells/75 cm flask) are released by brief trypsin treatment (rinsing with 0.05% trypsin) in physiologic salt solution containing 5 mM EDTA and 10 mM Hepes, pH 7.4 and resuspended in fresh medium containing actimonycin D (1 µg/ml). The cells are then plated in 96 well microtiter dishes ($5-7 \times 10^4$ cells/well).

After 2 hours in culture, serially diluted samples are added to wells, (less than 10–20% serum), and plates incubated overnight (5% $CO_2$, 37° C.). Samples are assayed in quadruplicate. The next day, following microscopic evaluation, the medium is decanted, and the wells filled with a solution of 0.2% crystal violet, 10% formalin and 0.01 phosphate pH 7–7.5 for 5 min., washed thoroughly with water and dried. The degree of lysis is quantitated spectrophotometrically (550–570 nM) on a microtiter plate reader. Assay results are expressed as U/ml, with one unit (U) defined as the amount of cachectin resulting in lysis of 50% of the cells.

In Vitro Neutralization Assay

Recombinant human cachectin (20 ng/ml in 0.02M Tris HCl, pH 8.0, 0.15M NaCl, 1 mg/ml BSA) is mixed with equal volumes of diluted antibody and incubated at 37° C. for 60 minutes. The mixture is diluted 1:10 with fresh medium containing actinomycin D (µg/ml); and 0.1 ml of serially diluted (two-fold) samples in quadruplicate is added to microtiter dish wells. The residual cytolytic activity is determined using the L929-cell cytotoxicity assay.

Characterization of Monoclonal Antibodies

Fourteen hybridomas positive for cachectin were identified and subcloned. The antibodies produced by these hybridomas were characterized for their ability to compete with monoclonal antibody 18-1-1 (obtainable from hybridoma ATCC Accession No. HB9228, Tracey et al, *Nature* (1987) 330:662–664, incorporated herein by reference) for cachectin binding in an ELISA. As shown in Table 1, the monoclonal antibodies fall into three classes; those that do not compete with 18-1-1, those that do, and those that show intermediate competition. To verify that those monoclonal antibodies which did not compete with 18-1-1 were specific for cachectin, a cachectin capture assay was performed. On a solid phase were bound the monoclonal antibodies to capture cachectin, and monoclonal antibody 18-1-1 was used as the labeled antibody. All the monoclonal antibodies were specific for cachectin by this assay.

Experiments with conditioned media from hybridoma cells were also performed to determine the extent the Mabs neutralized the cell killing activity of cachectin. All of the 14 monoclonal antibodies were produced in mouse ascites fluid for further characterization. The efficacy of the purified monoclonal antibodies in protecting L929 cells against killing by cachectin was determined. The neutralizing activity of MAb 1-2-4B1 had been confirmed with the purified material. Incubation of MAb 2-2-3E3 (50 ng/ml) with an equal volume of human recombinant cachectin (20 ng/ml) at 37° for 60 min., showed that 50% of the cytolytic activity of cachectin was neutralized as determined by the L929 cell killing assay. As shown in Table 1, MAb 2-2-3E3, which recognizes the same epitope as MAb 18-1-1, is required in ⅛ the amount of 18-1-1 for cell protection. Also shown in Table 1, is that most of the antibodies of the same specificity as 18-1-1 neutralized cachectin (at 50%) in the L929 cell killing assay. Other antibodies, such as 1-2-4B1, which have different epitope specificities from that of 18-1-1, also possessed significant neutralizing activity.

a two hour infusion of E. coli. A bolus injection of anti-TNF monoclonal antibody 2-2-3E3 F(ab')$_2$ fragment (10 mg/kg) was administered to four baboons at T+30 minutes (one-quarter of the way through the bacterial infusion, ie., "post-treatment") one additional baboon was given the same dose of E. coli plus gentamicin and treated with an isotype control of an irrelevant F(ab')$_2$ fragment.

(1) Survival Data

| DATE | EXPERIMENT | BABOON # | BABOON WT. (KG + SEX) | DOSE E. COLI (# ORG/KG) | SURVIVAL TIME |
|---|---|---|---|---|---|
| 2/25/88 | + Antibody | 1 | 6.8 M | $3.7 \times 10^{10}$ | 17 hours |
| 3/1/88 | + Antibody | 2 | 14.3 M | $4.6 \times 10^{10}$ | 24 hours |
| 3/17/88 | + Antibody | 3 | 7.3 M | $6.2 \times 10^{10}$ | 7+ days |
| 4/5/88 | + Antibody | 4 | 6.6 FM | $4.4 \times 10^{10}$ | 7+ days |
| 4/6/88 | Control (Carrier) | 5 | 6.4 FM | $6.5 \times 10^{10}$ | 21 hours |

TABLE 1

Profile of Monoclonal Antibodies Reactive with Human Cachectin

| Hybridoma | MAb, type[a] | Competition assay with 18-1-1[b] | Neutralization Assay Medium | Purified Ig, ng |
|---|---|---|---|---|
| 18-1-1 | IgG | + | + | 400 |
| 1-2-4D4 | IgG | + | + | |
| 1-2-4B2 | IgM | − | − | |
| 1-2-4B1[c] | IgG | − | + | 400 |
| 1-1-1F3 | IgG | − | ± | |
| 2-2-2FS | IgG | + | ± | >800 |
| 1-1-4C8 | IgG | − | ± | |
| 2-2-3E3[c] | IgG | + | + | 50 |
| 1-2-2F8 | IgG | + | + | |
| 1-1-2E3 | IgG | + | + | 200 |
| 1-2-2A1 | IgG | ± | + | |
| 2-3-1A8 | IgG | ± | + | |
| 1-2-4C6 | IgG | ± | − | |

[a]Determined by SDS-PAGE of MAb partially purified from ascites fluid by precipitation with ammonium sulfate.
[b]Determined in a Solid Phase Competition ELISA as follows. Conditioned medium from 24 hr hybridoma cultures (50 μl) and HRP-labelled 18-1-1 (25 μl, 0.2 μg/ml in PBS + 10% goat serum) were added to each well.
[c]The cell lines 1-2-4B1 and 2-2-3E3 were deposited with the American Type Culture Collection, 12301 Parklawn Drive, Rockville, Maryland 20852, on June 8, 1988 and designated Accession Numbers HB9737 and HB9736, respectively.

Efficacy of post-treatment with anti-TNF monoclonal antibody fragment in preventing the deleterious effects of sepsis in the baboon.

Baboons were intravenously administered a two hour $LD_{100}$ infusion of Escherichia coli (E. coli). Animals were monitored for 10 hours and observed until death, or for a maximum of 7 days. The aminoglycoside antibiotic, gentamicin, was administered at designated times following (2) Post-mortem observations Summary of post-mortem examinations conducted on baboons #1, 2, 5, (post-mortems not included on surviving baboons #3, 4 because prior work with surviving animals showed no adverse histological effects). The gross post mortem findings on animals #1, 2, 5 were very similar to each other and are as follows:

Lungs: Hemorrhagic
Kidneys: Congested, necrotic
Adrenals: Hemorrhagic, necrotic
Liver: Congested
Spleen: Engorged and congested
Intestines: Normal in appearance but intussusceptions in small intestine were observed in animals #1, 2.

Heart, pancreas, stomach, colon: Normal in appearance.

(3) Physiological and other parameters monitored for ten hours (a) Parameters associated with survival benefits in baboons #3, 4 and different from nonsurviving baboons (#1, 2, 5) were: ↑Mean systemic arterial pressure (MSAP), ↑pH, ↓lactate, ↓BUN, ↓creatinine, ↓SGPT, ↓cortisol, ↑glucose, ↓FDP and ↑fibrinogen.

(b) Parameters no different between surviving (#3, 4) and nonsurviving (#1, 2, 5) baboons were: Heart and respiration rates, WBS, platelets, $pCO_2$, $pO_2$, CPK, hematocrit, colony (E. coli) blood concentrations, body temperature.

When the studies were repeated with whole antibody, no significant differences were noted. Thus, both binding fragments and intact antibodies may be utilized in accordance with the present invention.

From the foregoing, it will be appreciated that the cell lines of the present invention provide means for producing monoclonal antibodies and fragments thereof reactive with human cachectin at low neutralizing amounts. This allows prophylactic and therapeutic compositions to be more economically developed and safely administered to be effective against infections due to most endotoxin bearing bacterial strains. In addition, the antibodies will find uses in various diagnostic and other therapeutic procedures.

Although the present invention has been described in some detail by way of illustration and example for purposes of clarity of understanding, it will be apparent that certain changes and modifications may be practiced within the scope of the appended claims.

I claim:

1. A composition comprising a monoclonal antibody produced by cell line 2-2-3E3 (A.T.C.C. Accession Number HB9736), or an F(ab')$_2$ fragment thereof which can immunologically bind human cachectin.

2. The cell line designated A.T.C.C. Accession Number HB9736.

3. A method of producing monoclonal antibodies that can neutralize cachectin comprising:

cultivating the cell line of claim 2 and recovering said antibodies.

4. The composition according to claim 1, wherein the antibody or F(ab')$_2$ fragment is conjugated to a label that provides a detectible signal.

5. The monoclonal antibody composition according to claim 4, wherein the label is a fluorescer or an enzyme.

6. A kit for the detection of endotoxin-bearing bacteria infection in a host, said kit comprising a monoclonal antibody composition that comprises monoclonal antibodies produced by a cell line designated ATCC Accession Numbers HB9736 or HB9737 and labels providing for a detectable signal covalently bonded to said monoclonal antibody or bonded to second antibodies reactive with said monoclonal antibody.

7. The composition of claim 1, further comprising a monoclonal antibody produced by cell line 1-2-4B1 (A.T.C.C. Accession Number HB9737).

8. The cell line designated A.T.C.C. Accession Number HB9737.

9. A method of producing monoclonal antibodies that can neutralize cachectin comprising:

cultivating the cell line of claim 8 and recovering said antibodies.

10. A method of inhibiting cachectin activity comprising:

(a) providing a monoclonal antibody produced by a cell line selected from the group consisting of cell line 2-2-3E3 (A.T.C.C. Accession Number HB9736) and cell line 1-2-4B1 (A.T.C.C. Accession Number HB9737); and (b) contacting cachectin with an amount of said monoclonal antibody that can inhibit cachectin activity.

* * * * *